United States Patent [19]
Reiss et al.

[11] Patent Number: 5,512,057
[45] Date of Patent: Apr. 30, 1996

[54] INTERFERENTIAL STIMULATOR FOR APPLYING LOCALIZED STIMULATION

[75] Inventors: Hans W. Reiss, Encinitas; Bernard Lafreniere, Carlsbad, both of Calif.

[73] Assignee: Medserv Group, Inc., Vista, Calif.

[21] Appl. No.: 337,773

[22] Filed: Nov. 14, 1994

[51] Int. Cl.$^6$ .............................. A61N 1/36; A61N 1/00
[52] U.S. Cl. ...................... 607/67; 607/62; 607/66; 607/70
[58] Field of Search ............................. 607/62, 66, 67, 607/68, 70, 72

[56] References Cited

U.S. PATENT DOCUMENTS

| | | | |
|---|---|---|---|
| 4,769,881 | 9/1988 | Pedigo et al. | 607/62 |
| 4,848,347 | 7/1989 | Hall | 607/67 |
| 5,161,530 | 11/1992 | Gamble | 607/67 |

*Primary Examiner*—Lee S. Cohen
*Assistant Examiner*—Stephen Huang
*Attorney, Agent, or Firm*—Frank D. Gilliam; John R. Duncan

[57] ABSTRACT

An interferential stimulation device for providing transcutaneous electrical nerve stimulation to a living body. The device applies current at two difference frequencies, each across two contact points on the body, spaced about a selected crossing point. The different frequencies produce at the crossing point a low frequency beat by the heterodyne process for specific stimulation at the crossing point. Electronic circuitry is provided to generate the desired signals and apply them through body contacting pads. Several modes for changing the stimulation smoothly, with the interference beat frequency ramped over a selected range over a selected time period provides superior results and prevents accommodation to the device. Several different ramp beat frequency ranges are provided, including a long range ramp, a relatively low frequency ramp and a relatively high frequency ramp.

4 Claims, 5 Drawing Sheets

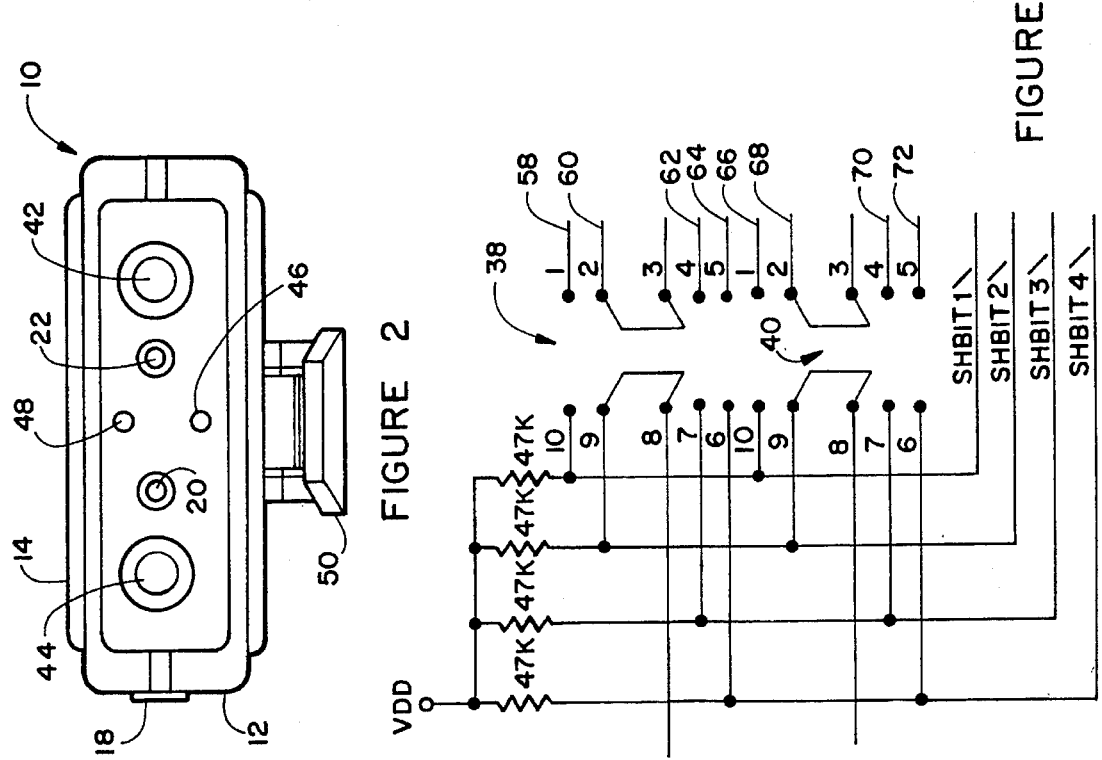
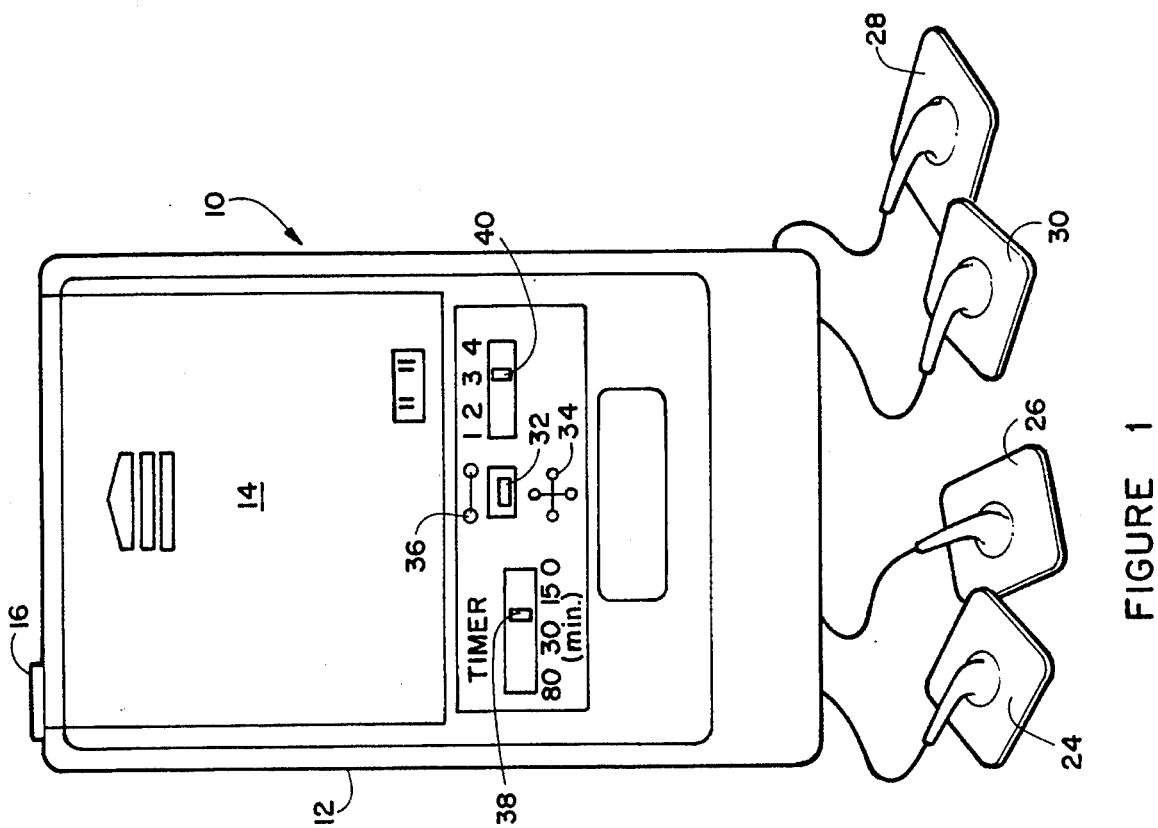

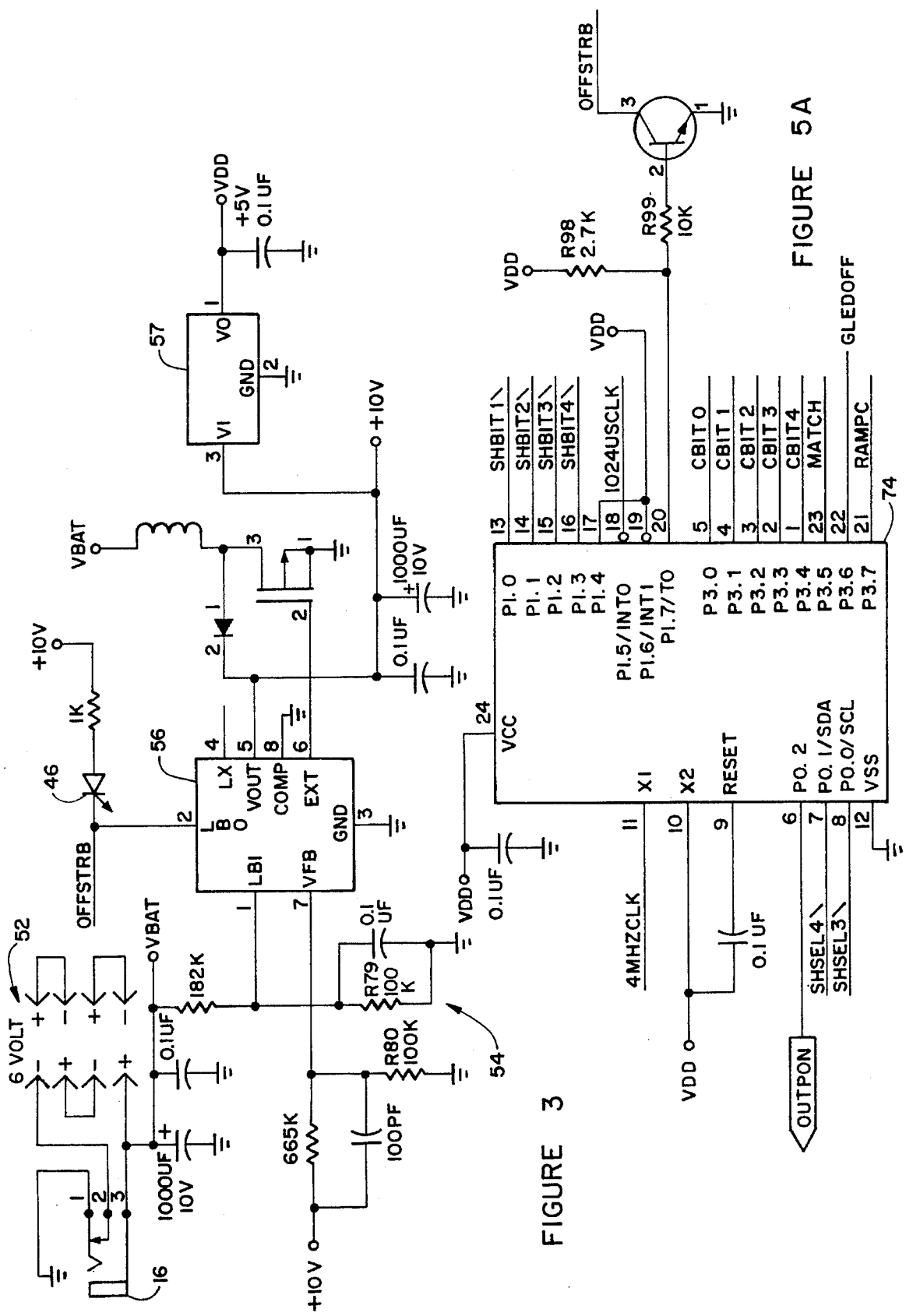

INTERFERENTIAL STIMULATOR FOR APPLYING LOCALIZED STIMULATION

BACKGROUND OF THE INVENTION

This invention relates in general to electrotherapy apparatus and, more specifically to an interferential generator for treating a living body with low frequency therapeutic current at a selected point with the ability to vary the current characteristics over selected time periods.

A wide variety of transcutaneous electrical nerve stimulation (TENS) devices have been developed to deliver electrical current to an area of a living body, typically a human being, to alleviate pain. Typical of these is the well-known system that applies a carrier signal to the skin through an electrode. The signal is in the form of D.C. bursts in the frequency range of 10,000 to 19,000 Hz, modulated on and off at a lower frequency. Other typical TENS type devices include the microprocessor controlled device for applying a low frequency pulse train and a modulated high frequency pulse train to a patient through an electrode as disclosed by Padjen et al in U.S. Pat. No. 4,719,922, a device in which a constant current square wave signal is directed into the body between two electrodes as described by Hudleson et al in U.S. Pat. No. 4,232,680 and a device in which a high frequency low amperage current is applied to a body through an electrode as described by Liss et al in U.S. Pat. No. 3,902,502.

The prior art TENS devices deliver a wide area stimulation, rather than the generally preferable localized stimulation. Also, prior art devices tend to provide a uniform signal throughout a treatment. The body tends to accommodate to the stimulation, lessening its effectiveness over time. While of varying effectiveness, these prior devices are not as effective as would be desired in treating pain and other conditions.

An interferential stimulator overcoming many of these problems is described and claimed in my prior U.S. Pat. No. 5,324,317. While highly effective, the stimulator of that patent does not provide certain operational advantages and the ability to vary current characteristics in certain ways that I have now found to be highly beneficial.

Thus, there is a continuing need for electrotherapy devices of improved effectiveness, which need is met by the interferential stimulator of this invention.

SUMMARY OF THE INVENTION

The interferential stimulation device of this invention delivers localized stimulation rather than broad area stimulation by the use of four contact points and two different frequencies that, at the crossing point, produce a low frequency beat by the heterodyne process for specific stimulation at the crossing point.

This device includes many of the controls provided in the stimulator described in my prior U.S. Pat. No. 5,324,317, plus the ability to smoothly vary or ramp the stimulation pattern over a selected time period. I have found that changing the sequence of stimulation smoothly, with frequency ramped over a selected range over time, provides superior results when compared to abrupt changes in frequency in preventing accommodation to the unit. Different ramp modes may be preferred for different patients and different conditions. Further, I have found that for treatment of different conditions it is beneficial to provide two significantly different ranges of stimulation, one over a selected milliamp range and the other over a selected microamp range.

Fixed frequency generation means generates a fixed frequency of from about 1000 to 10,000 Hz. Best results have been obtained at about 4000 Hz. An interference frequency generation means generates a selected frequency of up to about 1000 Hz different from the fixed frequency. Optimally, this frequency is up to about 200 Hz greater than the fixed frequency with a fixed pulse width of about 150 microseconds. This produces a beat frequency equal to the difference in the two generated frequencies, typically from about 1 to 150 beats per second. These beat frequency pulses preferably are biphasic generally sinusoidal wave pulses with a pulse width of from about 10 to 500 microseconds, with about 150 microseconds preferred. While any suitable ramp time period may be used, best results are obtained where the beat frequency is ramped from one end to the other end of the beat frequency range over up to about 20 seconds.

The interferential stimulator includes a mode control to permit changing the sequence of stimulation to prevent accommodation to the unit and to enable a number of alternatives to be evaluated to find the most effective pain relief. In the first mode, the unit is operated in a continuous manner at one set of frequencies with no change in pattern, with current application continuing for up to about up to about 20 seconds. In a second mode the stimulator typically operates over a full ramp range of about 0 to 200 beats/sec, with each ramp sequence taking about 1 to 20 seconds. A ramp range of about 1 to 150 beats/second, with each ramp sequence taking about 1 to 10 seconds giving optimum results. In a third mode, the stimulator operates at a high frequency ramp over a range, typically, of about 50 to 200 beats/sec, with optimum results over a range of about 80 to 150 and a ramp time period of about 1 to 200 seconds. In a fourth mode, the stimulator operates at a low frequency ramp over a typical range of up to about 20 beats/sec, with a range of about 1 to 10 providing optimum results and a ramp time period of from about 1 to 150 seconds. While the rate of change in beats per second may vary in any suitable manner, for best results a reasonably uniform rate of change, producing a substantially straight line ramp, is preferred.

Any suitable output voltage and amperage may be used. Preferably, two output current ranges are provided, one producing an output current range of up to 70 milliamps and the other up to 7 milliamps to provide, in effect, a microamp range, each with a load of about 500 ohms. The maximum output voltage range is up to 35 volts peak-to-peak for the milliamp range and up to 3.5 volts for the microamp range. The treatment may be continued for any suitable period, with the different modes used for different portions of the treatment, as desired. In general, treatments of up to about 60 minutes are preferred, with the time period controlled by a variable timer included in the unit.

For best results, four electrodes are used, one applying the fixed frequency, one applying the interference frequency and two ground or neutral electrodes. The electrodes are preferably arranged in a circular, square or other closed figure pattern with the application electrodes and ground electrodes alternating around the figure. This provides optimum localization of the stimulation at the center of the figure. If desired, the frequency mixing may be done internally, with the mixed signal being applied through one electrode spaced from a ground electrode.

BRIEF DESCRIPTION OF THE DRAWING

Details of the invention, and of certain preferred embodiments thereof, will be further understood upon reference to the drawing, wherein:

FIG. 1 is a plan view of the interferential stimulator of this invention;

FIG. 2 is an end elevation view of the interferential stimulator of FIG. 1;

FIG. 3 is a schematic circuit diagram basically showing the power supply portion of the stimulator circuit;

FIG. 4 is a schematic circuit diagram basically showing the control switch portion of the stimulator circuit;

FIG. 5A is a schematic circuit diagram basically showing the microcontroler portion of the stimulator circuit;

DETAILED DESCRIPTION OF PREFERRED EMBODIMENTS

Figures 5B, 6A:
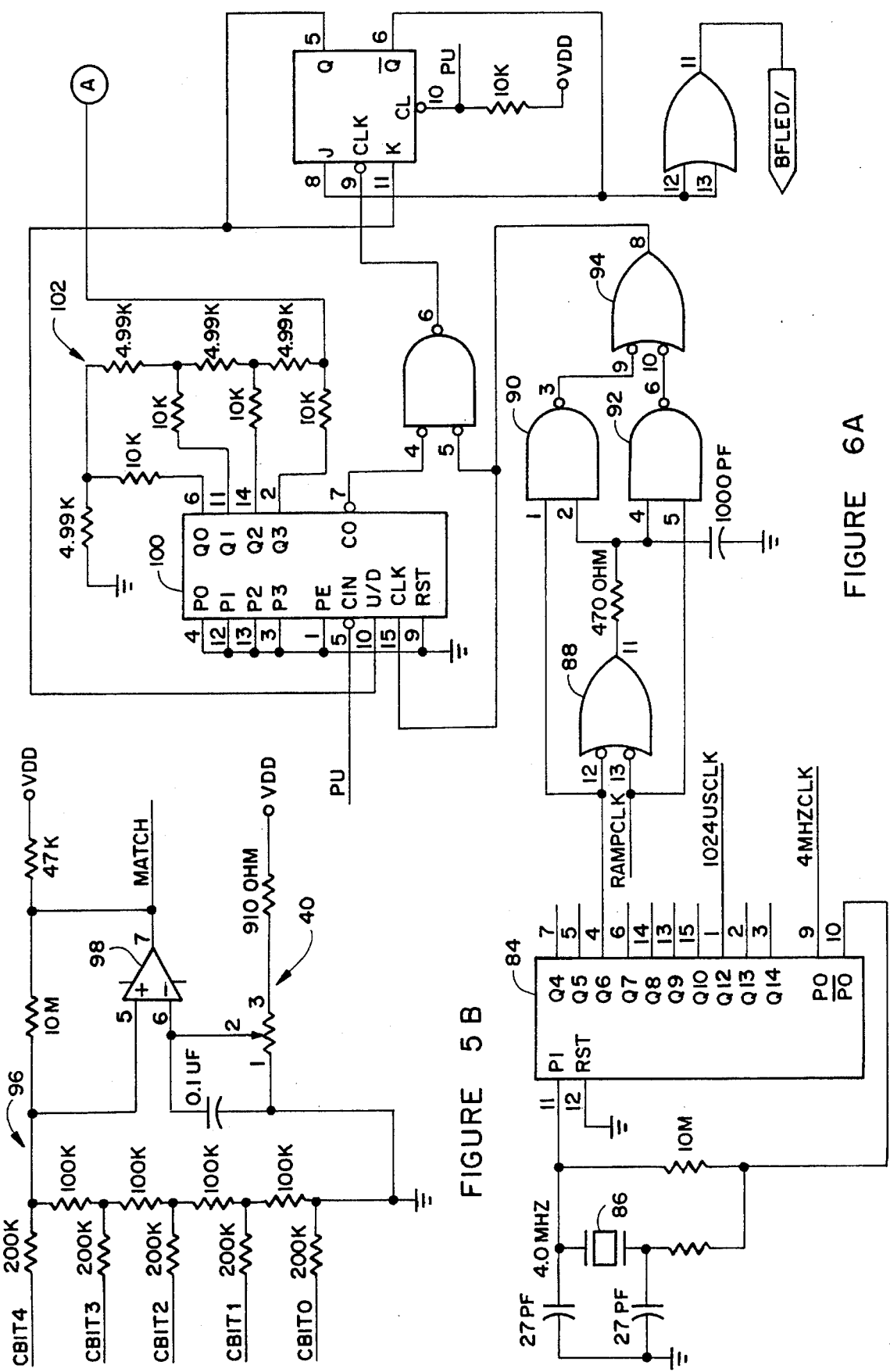
FIG. 5B is a schematic circuit diagram basically showing the digital to analog circuit associated with the microcontroler.
FIGS. 6A and 6B are schematic circuit diagrams basically showing the clock and wave generator portions of the stimulator circuit.

Referring now to FIGS. 1 and 2, there is seen an interferential stimulator 10 including a housing 12 containing the batteries and electrical components (not shown) and carrying various electrode jacks, indicator lights and operating switches. Towards the rear of the top of housing 12 is a cover 14 slidable to the rear to reveal the battery compartment which typically contains four AA batteries (not seen). A DC jack 16 may be provided for providing an external power source.

A pair of jacks 20 and 22 are provided in a recess on the front end panel for connection to the fixed frequency electrode 24 and the interference frequency electrode 26, respectively, and their associated ground or neutral electrodes 28 and 30. An electrode switch 32 on the top panel allows selection of the four electrode position (indicia 34) where interferential frequencies are mixed at the crossing point of the electrodes or the two electrode position (indicia 36) where the frequency mixing is done internally and only one of the jacks 22 is used.

A slide timer switch 38 is provided on the top panel. This switch can be set to "0" to allow the unit to run continuously, or to any time selected period, typically up to 60 minutes with selected intermediate settings. A mode switch 40 is provided to permit selecting which of the four operational modes is to be used, as detailed above. A rotary control 42 on the front panel is used to select the low frequency pulse rate, typically from about 1 to 150. A rotary control 44 is provided to set the signal amplitude A first light emitting diode 46 is provided on the front panel to indicate low battery conditions. A second light emitting diode 48 is a frequency indicator, connected to flash at the rate of the low frequency beat.

A conventional large plastic clip 50 is provided on the underside of the unit so that the unit may be clipped to the users belt or clothing. Thus, the unit is lightweight, compact and fully portable.

FIGS. 3–6 provide a preferred circuit for operation of the interferential stimulator. For convenience and clarity of illustration, the circuit has been divided into portions.

FIG. 3 basically shows the power supply portion of the circuit. An array 52 of battery contacts are provided for holding four conventional 1.5 volt batteries in series, providing the basic 6 volt power as required.

Battery voltage is applied to the VBAT input of IC 56 (a MAX642A from Maxim Integrated Products Inc), a DC to DC converter and regulator that operates over a wide range of voltage inputs and provides a 10 V output to various portions of the circuit and to IC 57 (a LM78L05 from Motorola), a 5 V regulator providing 5 V output (VDD) for use in other portions of the circuit.

An on-off switch is provided as part of amplitude control 44 as seen in FIGS. 1 and 2. Low battery detection circuitry 54, included with DC-to-DC converter 56, is provided to generate a "low battery" signal to LED 46 (FIG. 2) when the battery voltage drops to a selected level, typically 3.7 volts. Converter 56 generates +8 volts DC at output pin 5 for use at various places in the circuit. The +8 volts is also connected to the input of a voltage regulator 57, the output of which is +5 volts DC (indicated as "VDD") for use by microcontroller 74 and various IC's.

FIG. 4 shows the layout of the "on time" selection switch 38 and ramp clock mode selection switch 40. Switch 38 selects among "0", or constantly on position 58, a 15 second position 60, a 30 second position 62 and a 60 second position 64. Any other time periods may be used, if desired. Switch 40 selects among a low frequency ramp position 66, a high frequency ramp position 68, a full ramp position 70 and a constant position 72. These switches are connected to microcontroler 74 as seen in FIG. 5A.

FIGS. 5A and 5B show the microcontroller and associated digital to analog converter portions of the circuit. While any suitable microcontroller may be used, a 87C750 from Phillips is preferred. Microcontroller 74 provides the necessary timing and control for the generation of the variable signal through jack 22 (FIG. 3), the output "on" time periods, the "on time" selector and the mode control selection. The output from pin 6 of the microcontroler is the Output On signal to the base of transistor 76 (FIG. 7), typically a 2N4401 from Motorola, which in combination with transistor 78, typically a 2N4408 from Motorola controls the output on/off condition. That condition is selected by the "on time" selection switch 38 by turning on and off the VCC voltage to the output power amps, integrated circuits 80 (FIG. 7B) and 82 (FIG. 6B), each typically a TDA7052A from Phillips. The input signal to pin 18 of microcontroller 74 is the 1024 μS clock from the clock generator and is used for the interrupt timing control of the microcontroller.

Integrated circuit 84 (FIG. 6A), typically a 74HC4060 from Motorola, is a 14 bit binary counter and oscillator used to provided the necessary primary clocks required for system operation. A 4 Mhz crystal is connected between pins 11 and 10 of IC 84, forming a 4 Mhz oscillator for the binary counter. The 64 Khz output from pin 4 provides the primary signal for the channel 1 output 20 FIGS. 2 and 7). A 1024 μS clock-from pin 1 of IC 84 provides the interrupt timing for microcontroller 74. The 4 Mhz output from pin 9 of IC 84 provides the necessary 4 Mhz clock for microcontroller 74.

The output from pin 21 of microcontroler 74, the Ramp Clock signal, is connected to pin 13 of IC 88 (FIG. 6A), typically a dual 3-input NOR gate 74HCOO from Motorola. This signal along with the 64 Kc clock connected to pin 12 of IC 88, through IC's 90 and 92 (both typically additional 74HCOO NOR gates) generates the SUM Clock at the output pin 8 of IC 94, typically another 74HCOO, to generate the variable frequency for channel 2 at output 22 (FIGS. 7 and 2).

Control signals for the on time selection and mode control are connected at microcontroller 74 to pins 13 (P1.0), 14

(Pl.1), 15 (P1.2) and 16 (P1.3), with the on time control being selected by switch select 3 through microcontroller pin 7 to switch 38 (FIG. 4), with the mode control being selected by switch select 4 from microcontroller pin 8 to switch 40.

The variable output rate is controlled by an analog to digital converter circuit shown in FIG. 5B. This circuit consists of a resistor network 96 and an operational amplifier 98, typically a LM393 from National Semiconductor. The outputs from pins 1–5 of microcontroller 74 are connected to the resistor network 96, the top of which is connected to pin 5 of op-amp 98. The top panel control 40 (also, FIG. 1) is connected as a voltage divider with a variable arm of a typically 10Ω linear potentiometer connected to input pin 6 of op-amp 98. The output pin 7 of op-amp 98 is connected to pin 23 of microcontroller 74 to provide the variable frequency control of the RAMP clock.

Figures 6B, 7A:
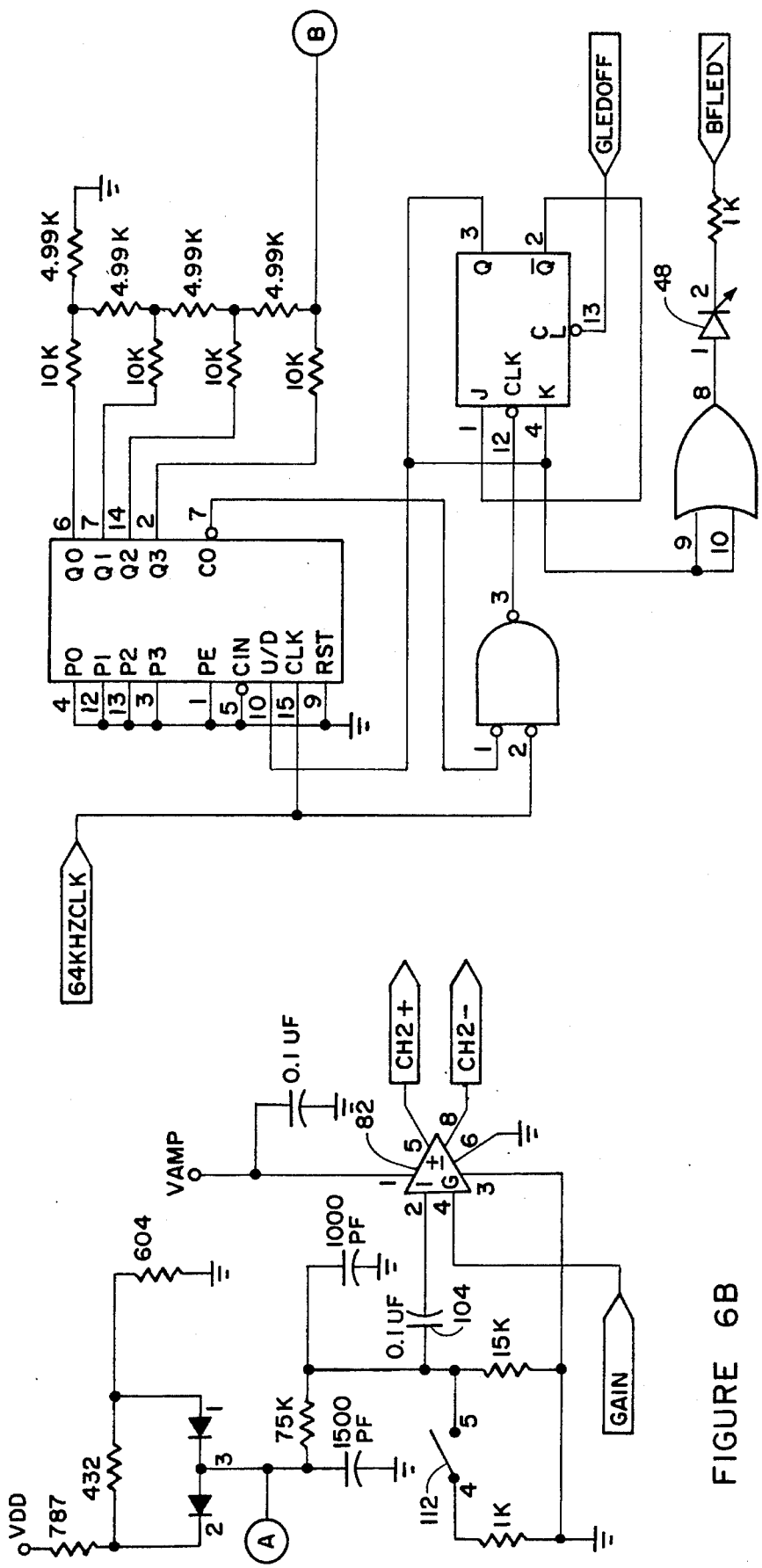
FIGS. 7A and 7B are schematic circuit diagrams basically showing the output portion of the stimulator circuit.
Figure 7B:
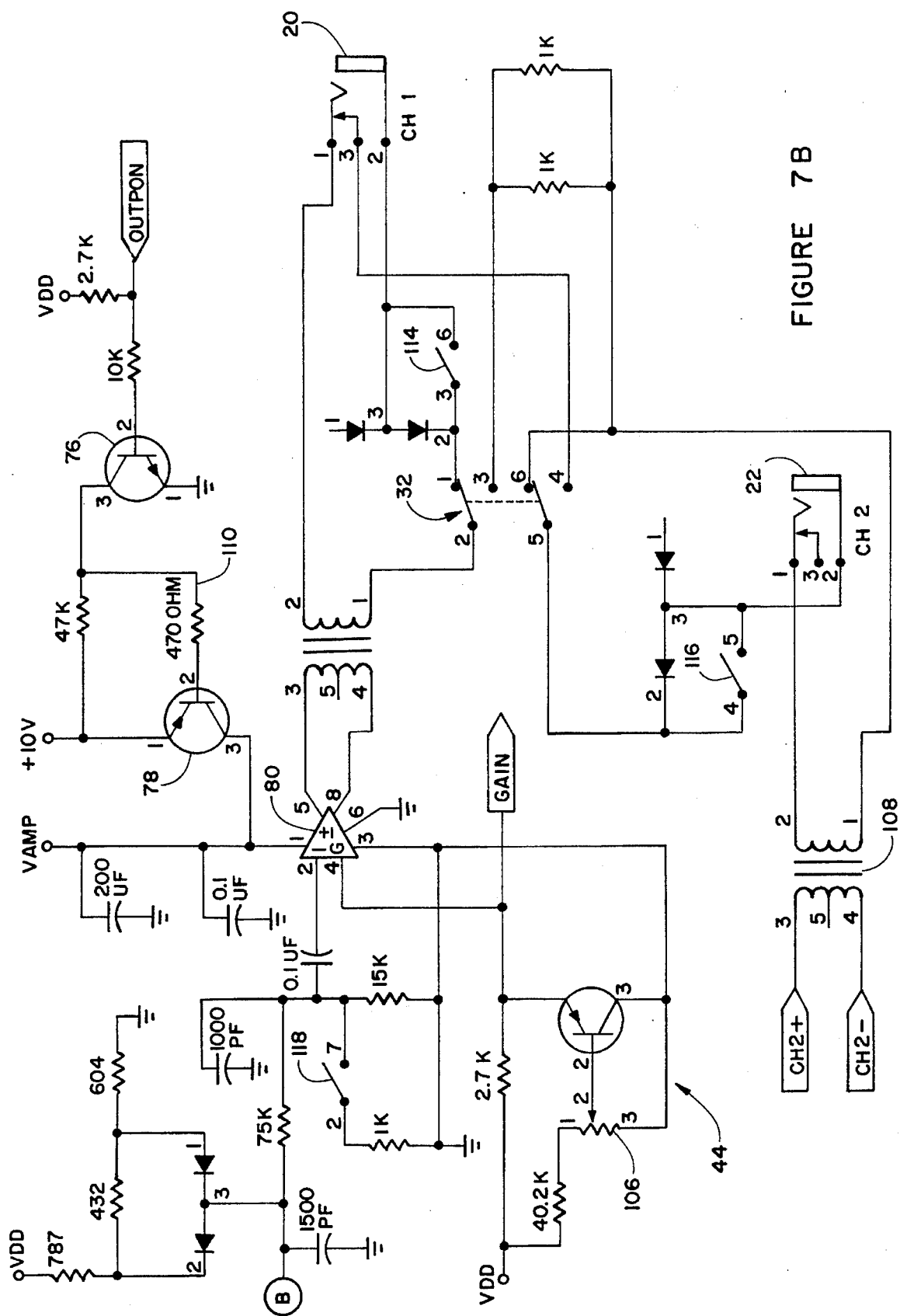

As seen in FIG. 6A, the channel 1 circuit has the 64 Khz clock signal from the clock generator IC's 84 and 88-94 connected to the clock input pin 15 of integrated circuit 100, a binary up/down counter, typically a 4516 from Motorola where the frequency division to the fixed output frequency occurs. The outputs of pins 6, 11, 14, and 7 are connected through a resistor ladder 102 and a capacitor 104 to the top end of the front panel amplitude control 44 (FIG. 2). As seen in FIG. 7, the variable arm of the amplitude (or gain) control 44 is connected to the input of the power amp 82 via a linear potentiometer 106. The output of power amp 82 (FIG. 6B) is connected through transformer 108 (FIG. 108) to the channel 1 output jack 20 (FIGS. 2 and 7) and the electrode selector switch 32 (FIGS. 1 and 7).

The circuit for channel 2 is the same as that for channel 1 with the exception that the variable input signal is derived from the Sumclock rather than the 64 Khz clock.

The control for the selection of microamp or milliamp output is controlled by the position of dip switch 112 (FIG. 6B). Switch 112 controls voltage to the input of the power amp shunt in the microamp position of switch 112 and reducing its output. Switches 112 (FIG. 6B) and switches 114, 116 and 118 (FIG. 7B) are ganged together to open and close together.

Electrode control switch 110 controls the connections to the output jack for channel 1 and 2. In the four wire position the jacks are isolated from each other and normal interferential stimulation occurs. In the two wire position, the outputs are mixed across 470Ω resistor 110 and both outputs have the same signal at a 1 to 150 Hz beat.

A beat frequency LED 48 (FIGS. 2 and 7) links at the frequency of the output signal beat, 1 to 150 Hz.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. In an interferential stimulator for delivering localized electrical stimulation to a living body which comprises fixed frequency signal generation means for generating a fixed frequency signal of up to about 10,000 Hz; at least one first electrode means for receiving said fixed frequency signal and imposing said fixed frequency signal on a skin surface of a living body; interference frequency signal generation means for generating a selected interference frequency signal up to about 1000 Hz different from said fixed frequency; at least one second electrode means for receiving said interference frequency signal and imposing said interference frequency signal on said skin surface at a location spaced a selected distance from said first electrode means to generate a selected interference pulse rate at a location below said skin surface; the improvement comprising:

microcontroller means for generating all circuit signals and timing;

means for selecting between a first output current range of from about 7 to 70 milliamps and a second output current-range of from about 7 to 70 microamps;

mode control means for controlling an operating mode of the stimulator including means for selectively providing any one of the following operating modes:
   (a) continuous application of a selected interference beat frequency of up to about 200 beats/sec;
   (b) operating at a continuously, substantially uniformly, varying beat frequency from one end to the other end of an entire range of frequency differences over a period of from about 1 to 20 seconds and repeating;
   (c) substantially uniformly varying the beat frequency over a ramp range from about 50 to 200 beats/sec over a period of from about 1 to 20 seconds and repeating;
   (d) substantially uniformly varying the beat frequency over a range from about 1 to 100 beats/sec over a period of from about 1 to 20 seconds and repeating.

2. The improvement according to claim 1 wherein said fixed frequency is about 4000 Hz and said interference frequency is from about 4001 to 4200 Hz.

3. The improvement according to claim 1 further including means for varying output current level within either of said milliamp and microamp ranges.

4. The improvement according to claim 1 wherein maximum outvoltage range is up to 35 volts peak to peak for said milliamp range and up to about 3.5 volts for said microamp range.

\* \* \* \* \*